(12) United States Patent
He et al.

(10) Patent No.: US 8,142,826 B2
(45) Date of Patent: Mar. 27, 2012

(54) **EXTRACT OF *FRAXINUS EXCELSIOR* SEEDS AND THERAPEUTIC APPLICATIONS THEREFOR**

(75) Inventors: Kan He, River Edge, NJ (US); Marc Roller, Morieres les Avignon (FR); Antoine Bily, Le Pontet (FR); Naisheng Bai, Highland Park, NJ (US); Jacques Dikansky, Avignon (FR); Alvin Ibarra, Hoboken, NJ (US)

(73) Assignee: Naturex, Inc., South Hackensack, NJ (US)

( * ) Notice: Subject to any disclaimer, the term of this patent is extended or adjusted under 35 U.S.C. 154(b) by 299 days.

(21) Appl. No.: 12/185,649

(22) Filed: Aug. 4, 2008

(65) Prior Publication Data

US 2009/0117214 A1      May 7, 2009

(51) Int. Cl.
*A61K 36/63* (2006.01)
(52) U.S. Cl. .......................... 424/771; 424/776
(58) Field of Classification Search .......... None
See application file for complete search history.

(56) References Cited

U.S. PATENT DOCUMENTS

| | | | |
|---|---|---|---|
| 2004/0096479 A1* | 5/2004 | Levine | 424/439 |
| 2004/0161524 A1 | 8/2004 | Sakai | |
| 2006/0089404 A1 | 4/2006 | Desai | |
| 2006/0189512 A1 | 8/2006 | Ehrenkranz | |

OTHER PUBLICATIONS

Maghrani (Journal of Ethnopharm. (2004), vol. 91, pp. 309-316).*
Silva (Food Sci. Tech Int. (2006), vol. 12, No. 5, pp. 385-396).*
Yang (Journal of Chinese Medicinal Materials (May 2007), vol. 30, No. 5, pp. 543-546).*
Calis, I., et al., A Secoiridoid Glucoside From *Fraxinus angustifolia*; Phytochemistry, 1996, vol. 41, No. 6, pp. 1557, 1559, abstract.
Maghrani, M., et al., Study of the Hypoglycaemic Activity of *Fraxinus excelsior* and *Silybum marianum* in an Animal Model of Type 1 Diabetes Milletus; J. Ethno-Pharmacology, Jan. 2004, vol. 91, pp. 309, 310.
Eddouks, M. et al., *Fraxinus excelsior* L. Evokes a Hypotensive Action in Normal and Spontaneous Hypertensive Rats; J. Ethno-Pharmacology, Mar. 19, 2005, vol. 99, pp. 49, 50, 53, Fig. 1, abstract.

* cited by examiner

*Primary Examiner* — Susan Hoffman
(74) *Attorney, Agent, or Firm* — Matthias Scholl, PC; Matthias Scholl

(57) ABSTRACT

A *Fraxinus excelsior* seed extract that can be administered for therapeutic treatment of a subject, including a human, by blocking fat synthesis, activating PPAR-alpha, increasing hypoglycemic activity, reducing bodyweight, controlling fasting plasma insulin levels against hyperinsulinemia, and promoting insulin sensitivity and causing a beneficial acute insulinotropic effect. The *Fraxinus excelsior* seed extract includes, inter alia, an isolated compound (2S,3E,4S) 2H-Pyran-4-acetic acid-3-ethylidene-2-[(6-O-β-D-glucopyranosyl-β-D-glucopyranosyl) oxy]-3,4-dihydro-5-(methoxycarbonyl)methyl ester, commonly called excelside A, an isolated compound (2S,3E,4S) 2H-Pyran-4-acetic acid-3-ethylidene-2-[(6-O-β-D-glucopyranosyl-β-D-glucopyranosyl)oxy]-3,4-dihydro-5-(methoxycarbonyl) 2-(4-hydroxyphenyl)ethyl ester, commonly called excelside B, and the compounds GI5, GI3, nuzhenide, and oleoside dimethyl ester.

7 Claims, 13 Drawing Sheets

1: EXCELSIDE A

2: EXCELSIDE B

3: NUZHENIDE

4: GI3

5: GI5

6: OLEOSIDE DIMETHYL ESTER

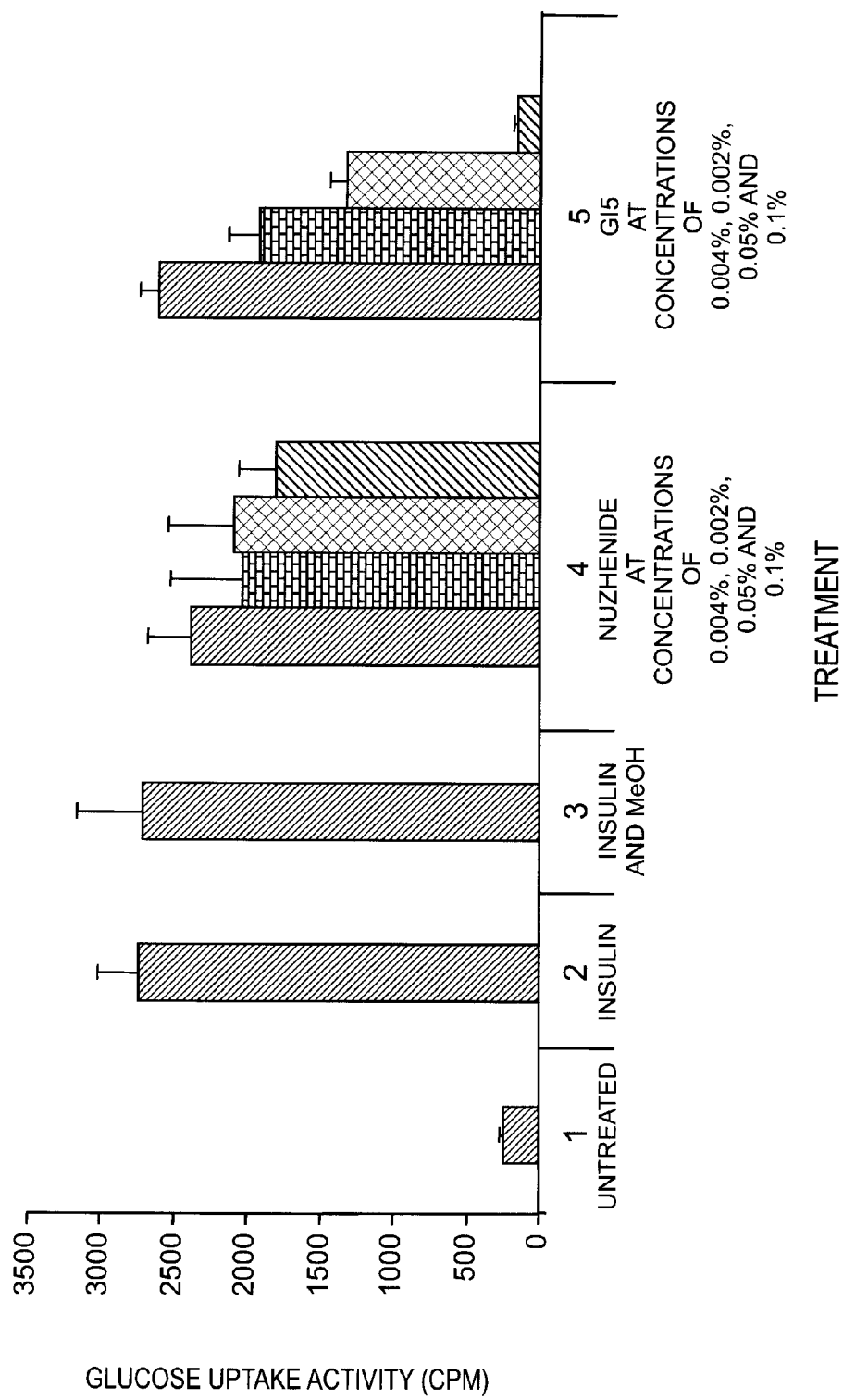

EXTRACT OF *FRAXINUS EXCELSIOR* SEEDS AND THERAPEUTIC APPLICATIONS THEREFOR

BACKGROUND OF THE INVENTION

Type 2 diabetes mellitus (DM-2) is a common global disease characterized by insulin deficiency and insulin insensitivity. DM-2 is considered to be a serious disease creating a health problem associated with a high morbidity and mortality, and is the sixth leading cause of death in the United States [Miniño et al, 2007, *National Vital Statistical Report*, 55]. It is expected that the number of diabetic patients could increase to 300 million worldwide by the year of 2025 [King et al, 1998, *Diabetes Care*, 21, 1414-31]. In the United States, 7 percent of the population—20.8 million children and adults—are affected by diabetes [French, 2007, *Inside*, 12, 46-7] and it costs the United States an estimated $132 billion in 2002 in medical expenditures and lost productivity [Hogan et al, 2003, *Diabetes Care*, 26, 917-32]. The treatment methods for DM-2 include use of insulin, insulin analogs or modified insulin, enhancing insulin release and insulin action, inhibiting hepatic glucose production, and inhibiting glucose uptake [Moller, 2001, *Nature*, 414, 821-27]. In addition to these therapeutic agents, traditional medicines for the treatment of DM-2 are also used throughout the world. More than 1,200 species of organisms have been used ethnopharmacologically or experimentally to treat symptoms of DM-2 [Marles and Farnsworth, 1996, *Protocol J. Botanical Med.*, 1, 85-137].

It is generally recognized that the rapidly rising prevalence of obesity represents a serious public heath problem in the United States. According to data from the 1999-2000 National Health and Nutrition Examination Survey (NHANES), nearly two-thirds (64.5%) of the adult population of the Unites States are overweight compared to 55.9% as detailed by the NHANES III research conducted between 1988 and 1994. The prevalence of obesity has also increased dramatically from 22.9% to 30.5% over the same period. The increasing number of obese people is likely at a high risk of developing a variety of obesity-related diseases include diabetes [Flegal et al, 2002, *JAMA*. 288, 1723-1727 and Kuczmarski et al 1994, *JAMA*. 272, 205-221].

*Fraxinus excelsior* L., a plant of the Oleaceae family, is commonly known as "Common Ash" or "European Ash" in the countries of temperate Asia and Europe [Gilman and Watson, 1993, *Fact Sheet ST*-264, November]. This plant is also widely distributed throughout Tafilalet, the southeastern region of Morocco, and is known there as "l'ssane l'ousfour." The Tafilalet region has been considered among the regions of Morocco where phytotherapy knowledge is the most developed [Eddouks et al, 2002, *J. Ethnopharmacol.* 82, 97-103]. Recent studies have indicated that *F. excelsior* (FE) possesses antibacterial and antioxidant activities. Methanol extract of FE showed potent antioxidant activity with $RC_{50}$ of $1.35 \times 10^{-2}$ in the qualitative α,α-diphenyl-β-picrylhydrazyl (DPPH) assay. The n-hexane and dichloromethane extract of FE were also active against eight species of Gram-positive and Gram-negative pathogenic bacteria tested including methicillin-resistant *Staphylococcus aureus* with minimal inhibitory concentration (MIC) values within $1.25 \times 10^{-1}$ mg/mL [Middleton et al, 2005, *Indian J. Pharma. Res.*, 2, 81-6]. The hypotensive effect of FE on both normotensive and spontaneously hypertensive rats was reported. Daily oral administration of the aqueous extract of FE seeds produced a significant decrease in systolic blood pressure and significantly enhanced the urination in both types of rats [Eddouks et al, 2005, *J. Ethnopharmacol.*, 99, 49-54]. The aqueous extracts of FE seed displayed potent hypoglycemic and antihyperglycemic activity in normal and streptozotocin-induced (STZ) rats without affecting basal plasma insulin concentrations [Maghrani et al, 2004, *J. Ethnopharmacol.*, 91, 309-16]. The Phlorizin-like effect of inhibition of renal glucose reabsorption might be one of the mechanisms for the hypoglycemic effect of FE [Eddouks et al, 2004, *J. Ethnopharmacol.*, 94, 149-54].

FE was reported to mainly contain coumarins, secoiridoids, and phenylethanoids. [Kostova and Iossifova, 2007, *Fitoterapia* 78, 85-106]. The secoiridoids found in FE are derived from oleoside. These types of secoiridoids exists only in plants of the family Oleaceae [Egan et al, 2004, *Biochem. Sys. Ecol.*, 32, 1069-71].

SUMMARY OF THE INVENTION

The present invention relates to novel secoiridoids that have been isolated from the seed extract of *Fraxinus excelsior* (common name Ash). The two compounds were identified as (1) (2S,3E,4S) 2H-Pyran-4-acetic acid-3-ethylidene-2-[(6-O-β-D-glucopyranosyl-β-D-glucopyranosyl)oxy]-3,4-dihydro-5-(methoxycarbonyl) methyl ester, named excelside A, having the chemical formula $C_{22}H_{32}O_{16}$ (FIG. 1-1); and (2) (2S,3E,4S) 2H-Pyran-4-acetic acid-3-ethylidene-2-[(6-O-β-D-glucopyranosyl-β-D-glucopyranosyl) oxy]-3,4-dihydro-5-(methoxycarbonyl) 2-(4-hydroxyphenyl)ethyl ester, named excelside B, having the formula $C_{30}H_{40}O_{17}$ (FIG. 1-2). Both compounds are oleoside-type secoiridoids characterized by an exocyclic 8,9-olefinic functionality.

The present invention also relates to a process of obtaining an isolated FE-derived composition. The composition can be obtained by a unique extraction and isolation process. The seeds are ground into granules with a particle size in a range from 0.1 mm to 30 mm to increase the surface area for the solvent to contact and to increase extraction efficiency. In one embodiment of the process, the temperature of extraction is in a range from 20° C. to 100° C. In a preferred embodiment, the temperature of extraction is in a range from 50° C. to 70° C. The ratio of plant material to solvent mixture used in the extraction process varies from 1:1 to 1:10 on a gram to milliliter basis. In one embodiment of the process, the ratio is from 1:3 to 1:8. The incubation period during which the plant material is in contact with the solvent mixture is for a period of time from about 2 hr. to about 24 hr. The extraction solvents can be water, a water-alcohol mixture (from 1% to 99% alcohol in water), and alcohol. The preferred alcohols are ethanol (EtOH) and methanol (MeOH). After the plant material and solvent have been incubated, the solvent is separated from residual plant material and the extraction composition is concentrated until the extraction composition has a solid component containing generally about 1%-35% of *F. excelsior* secoiridoids. The secoiridoids include two new oleoside-type glucosides, excelside A and excelside B, dimeric secoiridoids, nuzhenide (3) (FIG. 1-3), GI 3 (4) (FIG. 1-4), and GI 5 (5) (FIG. 1-5), as well as ligstroside, oleoside dimethyl ester (6) (FIG. 1-6), and oleoside-11-methyl ester. Other components include phenolic compounds, salidroside, coumarins, and flavonoids. After completion of the extract is formed, the secoiridoids are isolated. The secoiridoids can be isolated from the FE extract by a chromatographic process.

The secoiridoids are isolated from a dry powdered extract of FE. The powder is dissolved in an alcohol and the secoiridoids are extracted by alcohol from the powder. The alcohol is then evaporated and the remaining residue including secoiridoids is loaded into a chromatography column filled with reverse-phase C-18 resin. Several fractions containing different compounds are eluted with a series of water and 10% MeOH/90% water, and MeOH system. The fractions are compared by high performance liquid chromatography (HPLC) analysis and those elutes having similar HPLC patterns are combined. The combined fractions are separated on normal phase silica gel column chromatography and elute with chloroform ($CHCl_3$), $CHCl_3$-methanol mixture starting from 90%, 80% $CHCl_3$ to 100% MeOH to give several subfractions. The subfractions are compared by HPLC and the fractions which contain excelside A and excelside B are combined, respectively. The combined fractions are further purified by a combination of column chromatography over C-18, MCI GEL CHP-20P and/or Sephadex LH-20 resins to provide pure excelside A and excelside B.

The new chemical structures of excelside A and excelside B are elucidated using spectroscopic methods including nuclear magnetic resonance (NMR), ultraviolet (UV), infrared (IR), and mass spectroscopy (MS), and physical properties are also determined. The known chemical structures of secoiridoids are identified by direct comparison of the NMR spectra with those in the literature. The IR spectra were recorded on a Perkin-Elmer 1600 FTIR spectrophotometer using KBr plates. The NMR spectra were taken on a Varian INOVA 400 with deuterated methanol ($CD_3OD$) as the solvent. All the 2D-correlation spectra were obtained using standard gradient pulse sequences of Varian NMR software. The correlation spectra include COSY (Correlation Spectroscopy), TCOSY (Total Correlation Spectroscopy), HMQC (Heteronuclear Multiple Quantum Coherence), HMBC (Heteronuclear Multiple Bond Correlation), and ROESY (Rotating Frame Overhauser Enhancement Spectroscopy). The HPLC analysis was performed using an Agilent 1100 model HPLC system equipped with a quaternary pump, an autosampler, a four-channel-online degasser, a photodiode array detector, and Agilent Chemstation software. Molecular weights were determined using LC/MS ESI/APCI mode on a Finnigan LCQ ion trap mass spectrometer. UV spectra were acquired on a Schimadzu, UV-1700 UV-Visible Spectrophotometer.

The present invention also relates to the inhibitory effect of the two dimeric secoiridoids, GI5 (5) and nuzhenide (3) on an undifferentiated 3T3-L1 cell. The major component of weight gain is the deposition of adipose tissue in the body through an adipogenesis process. Adipogenesis is characterized by an increase in the number and size of fat cells. The inhibition of adipogensis by inhibiting fat cell synthesis to reduce the number and size of fat cells leads to control of bodyweight.

The present invention relates to the activation of PPAR-alpha by *Fraxinus excelsior* (FE) and the isolated secoiridoids from FE, oleoside dimethyl ester (6), excelside A (1), and GI3 (4). Peroxisome proliferator-activated receptors (PPARs) are nuclear receptors that control many cellular and metabolic processes. PPAR-alpha is expressed predominantly in liver where it has a crucial role in controlling fatty acid oxidation [Reddy and Hashimoto, 2001, *Annu Rev Nuir.*, 21, 193-230]. The induction of fatty acid oxidation by PPAR-alpha activation improves plasma lipid profiles. In a variety of mouse models, PPAR-alpha agonists lower plasma triglycerides, reduce adiposity and improve hepatic and muscle steaosis, consequently improving insulin sensitivity and reducing glucose in blood [Guerre-Millo et al, 2000, *J. Biol. Chem.*, 275, 16638-42 and Kim et al, 2003, *Diabetes*, 52, 1770-8].

The present invention also relates to the above composition, which is useful for treating metabolic syndromes to reduce blood glucose in a subject with DM-2, to aid in weight loss, and to balance the insulin level to prevent hyperinsulinemia, a symptom of insulin resistance in a DM-2 patient. When male C57BL/6J mice are fed a high-fat diet, they develop obesity, hyperglycemia, and hyperinsulinemia. Administration of an effective amount of FE can significantly decrease the glucose level in mice, reduce their bodyweight and body fat, and decrease plasma insulin levels.

In a human clinical trial, 16 fasting healthy volunteers were given 50 grams of glucose to induce postprandial glycemia and were administered FE or a placebo (wheat bran). The FE extract group lowered the incremental postprandial plasma glucose concentration as compared to placebo. It statistically (P=0.02) reduced the glycemic area under the blood glucose curve (AUC). The FE seed extract also induced a significant (P=0.002) secretion of insulin at 90 min after glucose administration.

BRIEF DESCRIPTION OF THE DRAWINGS

Further features, advantages and characteristics of the present invention will become apparent to a person of ordinary skill in the art in view of the following detailed discussion of preferred embodiments of the present invention, made with reference to the drawings annexed, in which:

FIG. 2 illustrates the glucose uptake activity (cpm) of compounds GI5 (5) and nuzhenide (3) for 1 untreated, 2, insulin, 3 insulin and MeOH, 4 nuzhenide at concentrations of 0.004%, 0.02%, 0.05%, and 0.1%; 5 GI5 at concentrations of 0.004%, 0.02%, 0.05%, and 0.1%;

FIG. 3 illustrates the relative activation of GAL4/PPARα fusion receptor by *Fraxinus excelsior* L. seed extract and 100 μM of fenofibrate (positive control) as compared with the effect of DMSO (control condition)(Values are mean±SD (n=4). *$P<0.05$, $P<0.01$; *$P<0.001$. Student's t test);

FIG. 4 illustrates results of fasting blood glucose (mg/dL) of low-fat (LF), high-fat (HF), and *Fraxinus* (HF+FE extract) treated mice after 16 week treatment;

FIG. 5 illustrates the results of average body weight (g) of low-fat (LF), high-fat (HF) and *Fraxinus* (HF+FE extract) treated mice at different weeks of treatment;

FIG. 6 illustrates relative PPARα activation potential (%) in reporter cell lines using concentrations ranging from $10^{-5}M$-$10^{-9}M$ for the selective synthetic PPARα activator WY14,643 as well as the isolated compounds at a concentration of 10 M and a 1:10 aqueous solution of FE seed extract, with compound label: FEI 9028 (Nuzhenide, 3), FE20015 (GI3, 4), FE20031 (oleoside dimethyl ester, 6), FE21008 (excelside A, 1), and FE21023 (GI5, 5);

DETAILED DESCRIPTION OF THE INVENTION

Figure 1:
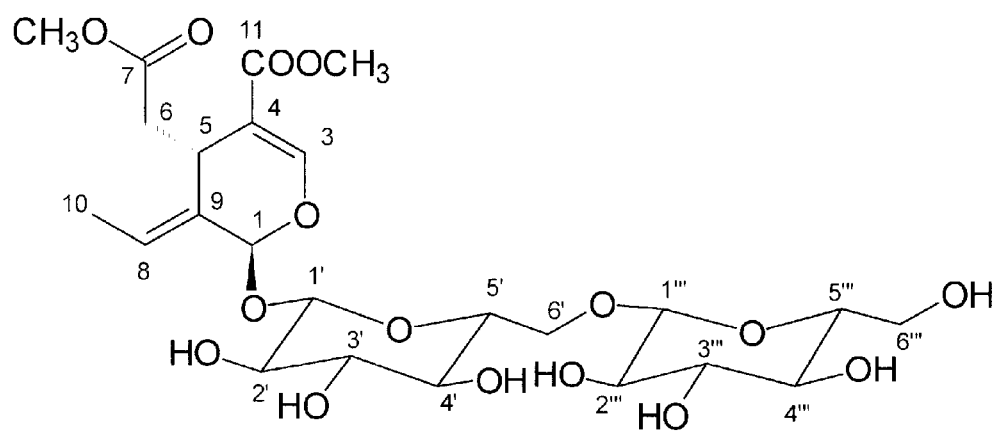
FIG. 1-1 through 1-6 illustrate the molecular structure of excelside A, excelside B, nuzhenide, GI3, GI5, and Oleoside dimethyl ester, respectively.

With reference to the drawings and the following examples, a preferred embodiment of the present invention for a *Franxinus excelsior* seed extract will now be described.

Example 1

Extraction of secoiridoids from *Fraxinus excelsior* with water. A total of 2.5 kg of the seeds of *F. excelsior* were dried in air and then ground into coarse powder with a particle size approximately 1-2 mm. The coarse powder was soaked in water in a percolator at 80-90° C. for 5 hours and the water extract was drained from the percolator. The extraction process was repeated three times. All the water extracts were combined together and concentrated in a rotary vacuum evaporator. After water was evaporated, a total of 550 grams of dried powdered extract was obtained. The HPLC analysis indicates that this powdered extract contained two major secoiridoids, 11.4% (weight/weight) of nuzhenide and 6.2% of GI3. The composition also contained 0.19% oleoside-11-methyl ester, 0.41% excelside B, 0.63% GI5, 0.2% salidroside, together with some minor secoiridoids including, ligstroside, oleoside dimethyl ester, and excelside A.

Example 2

Extraction of secoiridoids from *Fraxinus excelsior* with water, water-EtOH, and EtOH. 5 samples were prepared and each sample contained 5 grams of *F. excelsior* seeds. Each sample was milled into powder and was subjected to solvent extraction with 200 mL of water, 25% EtOH/75% water, 50% EtOH/50% water, 75% EtOH/25% water, and EtOH, respectively. After extraction for 24 hours at room temperature (22-24° C.), the solvents were evaporated and the residual solids were analyzed by HPLC. The secoiridoid contents and salidroside are listed in Table 1.

TABLE 1

Major secoiridoid contents and salidroside using different solvents (results expressed as percent by weight).

| Compounds | EtOH | 75% EtOH | 50% EtOH | 25% EtOH | water |
|---|---|---|---|---|---|
| Nuzhenide | 9.05 | 15.04 | 15.43 | 14.10 | 1.50 |
| GI 3 | 9.20 | 14.77 | 17.06 | 9.18 | 1.14 |
| Oleoside dimethyl ester | 0.57 | 0.91 | 0.78 | 0.74 | 0.96 |
| Excelside B | 0.06 | 0.09 | 0.10 | 0.12 | 0.03 |
| GI 5 | 0.91 | 1.45 | 1.70 | 0.83 | 0.10 |
| Salidroside | 0.08 | 0.17 | 0.16 | 0.18 | 0.74 |

Example 3

Isolation of secoiridoids from *F. excelsior*. 3.5 liters of methanol were added and mixed with 500 grams of powdered extract obtained from the procedure shown in Example 1, for 3 hours at room temperature. The methanol solution was separated from the powder by a filtration process. The same process was repeated once and the two methanol extracts were combined and concentrated under reduced pressure to yield a total of 54 grams of dried methanol extract. The methanol extract was re-dissolved in water and filtered to remove non-water soluble substances. The filtrate was further subjected to reverse-phase column chromatographic separation over C-18 resin washed with water and gradient MeOH-water solvent system from 10% MeOH in water to 100% MeOH. A total of 7 fractions were collected. Each fraction eluted from column was evaporated under vacuum and combined by HPLC analysis. Fractions 2, 3 and 7 were loaded on a chromatographic column filled with silica gel resin and eluted with chloroform-methanol system started from $CHCl_3$, 10% $MeOH/CHCl_3$, 20% $MeOH/CHCl_3$, to 100% MeOH. Fractions collected from silica gel column were compared by HPLC analysis and each separated eluate was repeatedly subjected to column chromatographies over MC1 GEL CHP-20P and/or Sephadex LH-20 resins and eluted with water-methanol system until a single pure compound was obtained. Two new compounds, excelside A and excelside B, together with several known compounds, nuzhenide, GI3, GI5, ligstroside, oleoside dimethyl ester, oleoside-11-methyl ester, and salidroside were discovered. All the chemical structures were elucidated by spectroscopic methods.

Example 4

Structure elucidation of excelside A and excelside B: Excelside A (1) was obtained as an amorphous powder. Its molecular formula $C_{22}H_{32}O_{16}$ was determined on the basis of its MS and confirmed by $^1H$ and $^{13}C$ NMR data (Table 2). The UV spectrum showed a typical absorption at 232 (sh) nm derived from an iridoidic enol ether system conjugated with a carbonyl group. The IR spectrum exhibited functional groups of hydroxyl at $v_{max}$ 3401, ester at 1734, 1717 and α,β-unsaturated ester 1626 cm$^{-1}$. Detailed analysis of its $^1H$, $^{13}C$-NMR and 2D correlation spectra indicated excelside A bearing an oleoside-type secoiridoid glucoside moiety which was supported by the proton signals at $δ_H$ 7.51 (s, H-3), 5.93 (s, H-1), 6.08 (qd, J=7.2, 0.8 Hz, H-8), 1.72 (d, J=7.6 Hz, $H_3$-10) and 4.80 (d, J=8.0 Hz, H-1), the corresponded carbon-13 signals at $δ_C$ 155.2 (C-3), 94.8 (C-1), 124.7 (C-8), 13.6 (C-10) and 100.5 (C-1'). Two methoxyl signals at $δ_H$ 3.62 ($OCH_3$, $δ_C$ 51.9) and 3.70 ($OCH_3$, $δ_C$ 52.3) showed correlation with C-7 ($δ_C$ 173.7) and C-11 ($δ_C$ 168.6) in the gHMBC spectrum, respectively, indicating excelside A having a 7,11-oleoside dimethyl ester unit [Boros and Stermitz, 1991, *J. Nat. Prod.*, 54, 1173-246]. Other than this, the appearance of additional NMR signals due to a β-glucopyranosyl moiety ($δ_C$ 100.6, 77.6, 77.8, 71.6, 75.3 and 70.1), suggested excelside A as a 7,11-oleoside dimethyl ester bearing with another glucosyl. The position of the glucosyl was determined to be attached at C-6' of the oleoside moiety since there was a downfield shift of 7.5 ppm of the signal at C-6' and upfield shifts of 0.5 and 2.6 ppm at C-3' and C-5', respectively, when compared to excelside A with the same position of the signal of 7,11-dimethyl oleoside. This deduction was further supported by gHMBC correlation spectrum, in which cross-peaks were observed between H-1''' at $δ_H$ 4.35 and C-6' at $δ_C$ 70.1 ppm, as well as between H-6' ($δ_H$ 4.15 & 3.84 ppm) and C-1''' ($δ_C$ 105.3 ppm). A methyl group was positioned to an E-configuration at 8,9-olefinic bond and was supported by ROESY spectrum where a strong correlation between H-10 ($δ_H$ 1.72) and H-5 ($δ_H$ 3.96) was observed. In the same spectrum, a correlation between H-10 ($\delta_H$ 5.93) and H-6 ($\delta$2.51) suggested glucosyl at C-1 adopted #-configuration. Hence, the structure of excelside A was determined to be (2S,3E,4S) 2H-Pyran-4-acetic acid-3-ethylidene-2-[(6-O-β-D-glucopyranosyl-β-D-glucopyranosyl)oxy]-3,4-dihydro-5-(methoxycarbonyl)methyl ester, named excelside A. The complete $^1$H and $^{13}$C NMR data assignments are given in Table 2.

Excelside B (2) was isolated as a colorless amorphous powder. Its molecular formula was determined as $C_{30}H_{40}O_{17}$ by MS and confirmed by NMR data. In the UV spectrum of 2, besides the typical absorption at 230 nm of an iridoidic enol ether conjugated with a carbonyl group, the additional absorptions at 275 and 283 nm indicated the existence of a phenol. IR showed hydroxyl at $v_{max}$ 3400, +,β-unsaturated ester at 1701, 1636, and aromatic ring at 1518 cm$^{-1}$. The $^1$H NMR and $^{13}$C spectra of excelside B displayed the typical signals due to an oleoside moiety: the olefinic signal at $\delta_H$ 7.50 (s, H-3), $\delta_C$ 155.2 (C-3), an allylic acetal at $\delta_H$ 5.94 (s, H-1), $\delta_C$ 94.7 (C-1), an anomeric signal from glucosyl at $\delta_H$ 4.82 (d, H-1'), $\delta_C$ 100.3 (C-1'), an olefinic proton from ethylidene group at $\delta_H$ 6.05 (d, H-8), $\delta_C$ 124.8 (C-8) and methyl from the ethylidene at $\delta_H$ 1.61 (d, H$_3$-10), $\delta_C$ 13.6 (C-10). The observed phenylethanoid signals as well as an AA'BB' spin system in the aromatic ring at $\delta_H$ 6.71 (2H, dd, J=6.8, 2.8 Hz) and $\delta_H$ 7.02 (2H, dd, J=6.8, 2.8 Hz) suggested apara-substituted pattern of the phenylethanoid. The long-range $^1$H-$^{13}$C correlation found in gHMBC between H-1" at $\delta_H$ 4.26 and C-7 at $\delta_C$ 67.0 ppm suggested that the phenylethanol was attached at the C-7 position, which related the structure of excelside B to ligstroside, a para-hydroxyphenylethanol methyl oleoside ester [Takenaka et al, 2000, *Phytochemistry*, 55, 275-84]. Similar to excelside A, the apparent additional β-glucopyranosyl unit in excelside B was suggested to be attached at C-6'. This was confirmed by a downfield chemical shift of 7.3 ppm by C-13 signal at C-6' of excelside B and upfield shifts of 0.7 and 2.9 ppm at C-3' and C-5', respectively, when compared with those of ligstroside. A further confirmation of such connection was observed in gHMBC spectrum where the strong correlation between the anomeric signal from the glucosyl at $\delta_H$ 4.31 (H-1''') and at $\delta_C$ 70.1 (C-6'). The position of the methyl group was assigned at C-11 due to the observed long-range cross-peak of the signals at $\delta_H$ 3.69 (OCH$_3$) and $\delta_C$ 168.7 (C-11) in the gHMBC spectrum. Thus, compound excelside B was designated as (2S,3E,4S) 2H-Pyran-4-acetic acid-3-ethylidene-2-[(6-O-β-D-glucopyranosyl-β-D-glucopyranosyl)oxy]-3,4-dihydro-5-(methoxycarbonyl) 2-(4-hydroxyphenyl)ethyl ester, named excelside B. The $^1$H and $^{13}$C NMR data assignments are given in Table 2.

TABLE 2

$^1$H, $^{13}$C NMR and HMBC data for compounds excelside A (1) and excelside B (2) (CD$_3$OD)

| No. | 1 $\delta_H$ | 1 $\delta_C$ | 1 HMBC (H to C) | 2 $\delta_H$ | 2 $\delta_C$ | 2 HMBC (H to C) |
|---|---|---|---|---|---|---|
| 1 | 5.93 s | 94.8 d | 8, 1' | 5.94 s | 94.7 d | 8, 1' |
| 3 | 7.51 s | 155.2 d | 1, 4, 5, 11 | 7.50 s | 155.2 d | 1, 4, 5, 11 |
| 4 | | 109.3 s | | | 109.3 s | |
| 5 | 3.96 dd (9.0, 4.3) | 31.9 d | 1, 3, 4, 6, 7, 8, 9, 11 | 3.95 dd (9.6, 4.0) | 32.0 d | 7, 11 |
| 6 | 2.76 dd (14.4, 4.4) | 41.1 t | 4, 5, 7, 9 | 2.72 dd (14.0, 4.0) | 41.3 t | 7 |
| | 2.51 dd (14.0, 10.0) | | 4, 5, 7, 9 | 2.50 dd (14.0, 9.6) | | 7 |
| 7 | | 173.7 s | | | 173.4 s | |
| 8 | 6.08 dq (7.2, 0.8) | 124.7 d | 1, 5, 10 | 6.05 d (6.8) | 124.8 d | 1, 5, 9, 10 |
| 9 | | 130.4 s | | | 130.1 s | |
| 10 | 1.72 d (7.6) | 13.7 q | 8, 9 | 1.61 d (7.2) | 13.6 q | 8, 9 |
| 11 | | 168.7 s | | | 168.7 s | |
| OCH$_3$ | 3.70 s | 52.3 q | 11 | 3.69 s | 51.9 q | 11 |
| OCH$_3$ | 3.62 s | 51.9 q | 7 | | | |
| 1' | 4.80 d (8.0) | 100.6 d | 1 | 4.82 d (7.6) | 100.4 d | 1, 2' |
| 2' | 3.24-3.68 m | 77.6 d | | 3.12-3.55 m | 77.5 d | |
| 3' | 3.24-3.68 m | 77.8 d | | 3.12-3.55 m | 77.8 d | |
| 4' | 3.24-3.68 m | 71.6 d | | 3.12-3.55 m | 71.5 d | |
| 5' | 3.24-3.68 m | 75.3 d | | 3.12-3.55 m | 75.1 d | |
| 6' | 4.15 dd (12.0, 1.6) | 70.1 t | 1''' | 4.15 d (10.4) | 70.1 t | 5', 1''' |
| | 3.84 br. d (12.0) | | | 3.81 dd (11.6, 2.4) | | |
| 1" | | | | 4.26 m | 67.0 t | 7, 2" 3" |
| | | | | 4.06 m | | 7, 2", 3" |
| 2" | | | | 2.80 t (6.8) | 35.2 t | |
| 3" | | | | | 130.3 s | |
| 4" | | | | 7.02 dd (6.8, 2.8) | 131.1 d | 2", 3", 6" |
| 5" | | | | 6.71 dd (6.8, 2.8) | 116.4 d | 3", 4", 6" |
| 6" | | | | | 157.0 s | |
| 7" | | | | 6.71 dd (6.8, 2.8) | 116.4 d | |
| 8" | | | | 7.02 dd (6.8, 2.8) | 131.1 d | |
| 1''' | 4.35 d (8.0) | 105.2 d | 6' | 4.31 d (8.0) | 105.2 d | 6' |
| 2''' | 3.24-3.68 m | 74.7 d | | 3.12-3.55 m | 74.7 d | |
| 3''' | 3.24-3.68 m | 77.7 d | | 3.12-3.55 m | 77.6 d | |
| 4''' | 3.24-3.68 m | 71.5 d | | 3.12-3.55 m | 71.4 d | |
| 5''' | 3.24-3.68 m | 77.8 d | | 3.12-3.55 m | 77.6 d | |
| 6''' | 3.98 dd (9.6, 4.4) | 62.7 t | | 3.74 dd (12.0, 6.8) | 62.6 t | |
| | 3.75 dd (12.0, 6.8) | | | 3.62 dd (12.0, 6.8) | | |

Chemical shifts δ expressed in parts per million (ppm) versus tetramethylsilane (TMS) as reference standard; signal multiplicity is reported as singlet (s), doublet (d), triplet (t), quartet (q), doublet of doublet (dd), doublet of quartet (dq), and multiple (m); coupling constant in the parentheses expressed as Hz; the solvent employed for taking NMR spectra is $CD_3OD$.

Example 5

Figures 1, 2:
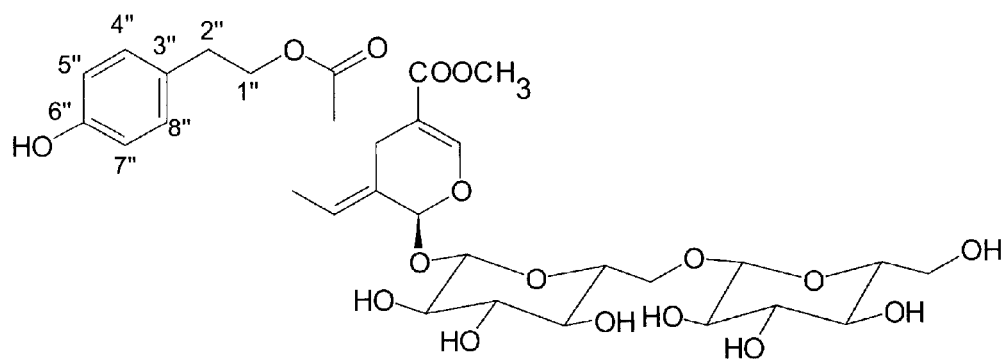

Inhibitory effect of GI5 (5) and nuzhenide (3) on undifferentiated 3T3-L1 cells. The major component of weight gain is deposition of adipose tissue in body through the adipogenesis process. Adipogenesis is characterized by increase in the size and number of fat cells. The secoiridoids, GI5 and nuzhenide isolated from *F. excelsior*, have shown significant and mild adipogenesis inhibitory activity, respectively, by blocking the pathway from undifferentiated 3T3-L1 cell to differentiated adipocyte to achieve an effect on bodyweight control and body fat loss. 3T3-L1 preadipocytes were induced to differentiate with methylisobutylxanthine, dexamethasone, and insulin (MDI) hormonal cocktail in the presence or absence of compounds. Ten days after differentiation induction, the treated cells were assayed for their respective glucose uptake activity, which is an indirect measurement of differentiation (adipogenesis) because preadipocytes are incapable of insulin-induced, glucose transport-4 (GLUT4)-mediated glucose uptake while fully differentiate adipocytes are capable of this uptake. Compounds, GI5 and nuzhenide, were used at four different concentrations: 0.004%, 0.02%, 0.05%, and 0.1%. Untreated (undifferentiated) cells were used as a negative control while insulin was used as a positive control. Methanol (MeOH), the solvent of the compounds, was also used as a control. The result showed that GI5 and nuzhenide isolated from *F. excelsior* possess significant and mild adipogenesis inhibitory activity, respectively, by blocking the pathway from undifferentiated 3T3-L1 cell to differentiated adipocyte to achieve an effect on bodyweight control and body fat loss (see FIG. 2).

Example 6

Figures 1, 2, 3:
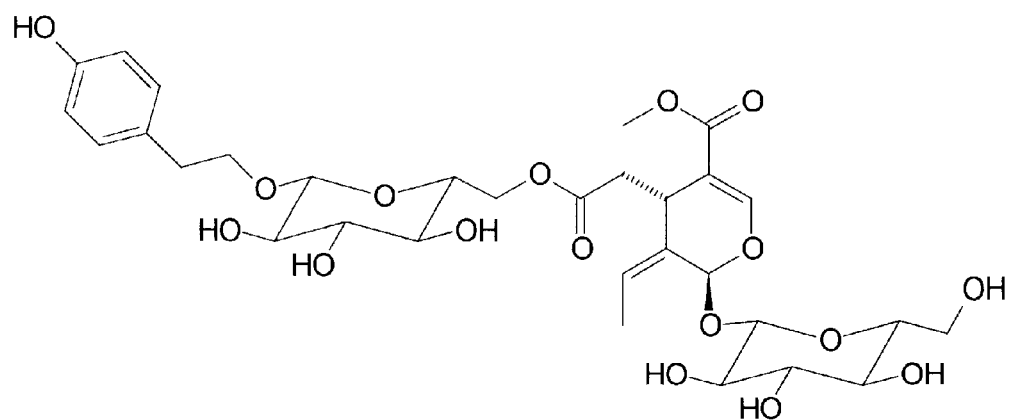

PPAR-alpha activation of *Fraxinus excelsior*. Peroxisome proliferator-activated receptors (PPARs) are nuclear receptors that control many cellular and metabolic processes. PPAR-alpha is expressed predominantly in the liver and where it has a crucial role in controlling fatty acid oxidation (Reddy and Hashimoto, 2001, *Annu Rev Nutr.*, 21, 193-230). The induction of fatty acid oxidation by PPAR-alpha activation improves plasma lipid profiles. In a variety of mouse models, PPAR-alpha agonists lower plasma triglycerides, reduce adiposity and improve hepatic and muscle steaosis, consequently improving insulin sensitivity and reducing glucose in blood [Guerre-Millo et al, 2000, *J. Biol. Chem.*, 275, 16638-42 and Kim et al, 2003, *Diabetes*, 52, 1770-8]:

*Fraxinus excelsior* seed extract obtained by using water as a solvent as described in Example 2 (FE extract) has been demonstrated to activate PPAR-alpha. The relative activations of PPAR-alpha by FE extract and fenofibrate (positive control) as compared with DMSO (control condition) were calculated as the luminescence signal of luciferase (a gene reporter) obtained from the active compounds after incubation with GAL4/PPAR-alpha receptor transfected cells. First, COS-7 cells (cultured in DMEM+10% FCS) were transiently transfected with a fusion protein GAL4/PPAR-alpha and a DNA construct carrying luciferase. For the transfection, first the plasmid pGAL5-TK-pGL3 was obtained by inserting five copies of the GAL4 (yeast transcription factor) DNA binding site in front of the thymidine kinase promoter of the pTK-pGL3 plasmid. Then, the plasmid pGAL4-hPPAR-alpha was constructed by PCR amplifying the hPPAR-alpha DEF domains (aal 80-464). The resulting PCR products were cloned in pBD-GAL4 (Stratagene, La Jolla, USA) and the chimera subsequently subcloned into the pcDNA3 vector. After transfection, COS-7 cells were incubated for 24 h with 0 μg/mL (control condition), 1 μg/mL, 3 μg/mL, 10 μg/mL, 30 μg/mL, 100 μg/mL, 300 μg/mL, and 1,000 μg/mL of FE extract, or 100 μM of fenofibrate (positive control). DMSO was used as the solvent. After incubation, cells were collected and a luciferase assay was performed. The activation of PPAR-alpha by FE extract and fenofibrate resulted in the expression of luciferase and consequent increment of the luminescent signals, which were measured with a Tecan Ultra Spectrophotometer (Tecan, Austria). Results were expressed as the relative activation of GAL4/PPAR-alpha proportional to the luminescent signal emitted as a result of the FE extract and fenofibrate as compared to the luminescent activity of the control (DMSO). Results are reported as the mean±SD of four trials for each test (FIG. 3). Differences between groups were calculated using Student's t-test (XLSTAT 2008, Add-insoft™, USA). The results of PPAR-alpha activation by FE extract is shown in FIG. 3. FE extract reached 18% of PPAR-alpha activation at 1.000 μg/mL. The results are expressed as a percentage of fenofibrate, an activator of PPAR-alpha used as a reference compound.

The capacity of FE extract to activate PPAR-alpha could explain, in part, the lowering glycemic effect observed in animal studies.

Example 7

Hypoglycemic activity of FE extract on male C57BL/6J mice. Male C57BL/6J mice were divided into three groups: 1) negative control group where 20 male mice were on low-fat diet (LF) with about 10 kcal daily intake; 2) positive control group where 20 mice were fed with high-fat diet (HF) and about 60 kcal daily intake and due to high-fat feeding, this group of mice developed obesity, hyperglycemia, and hyperinsulinemia; 3) 0.5% FE extract group where 10 male mice were fed with high-fat diet like those in group 2, but the diet was also mixed with 0.5% of FE extract. Food and fluid intake and body weight were measured weekly. Signs of abnormality and possible toxicity were monitored. Blood was sampled from the tail vein and fasting blood glucose level was measured using a blood glucose meter. Basal data was determined before the experiment. There was no statistical difference among the three groups.

Figures 1, 2, 3, 4:
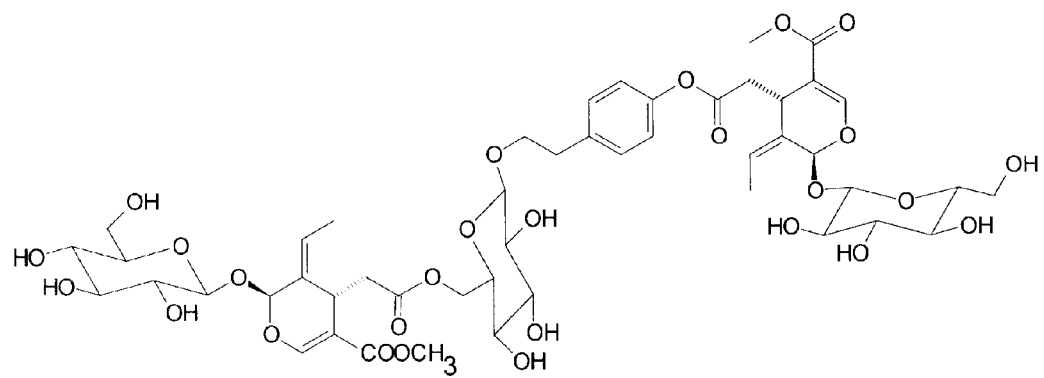

After 16-weeks of treatment, mice in the group treated with FE extract showed significantly lower fasting blood glucose levels than the mice in the high-fat control group (p<0.001), which indicated a strong hypoglycemic effect of FE extract (FIG. 4).

Example 8

Figures 1, 2, 3, 4, 5:
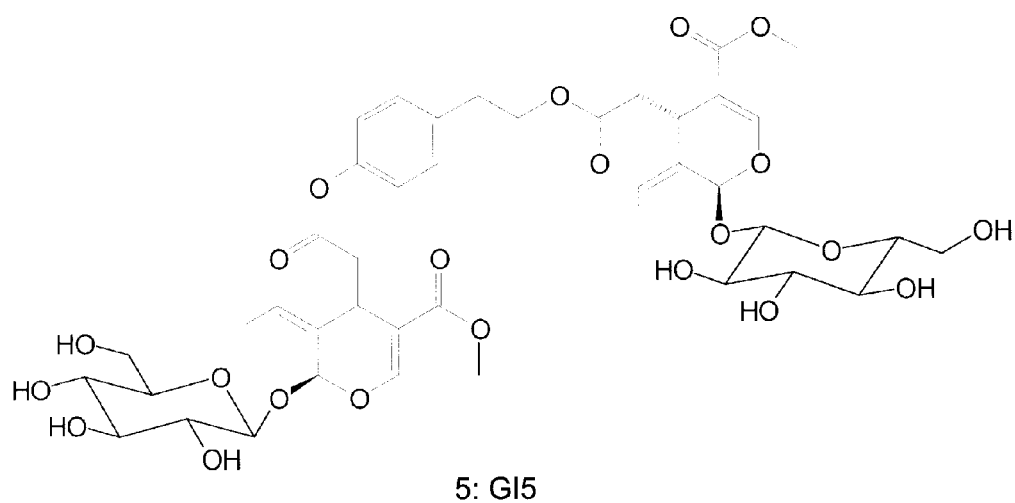

Bodyweight-reducing activity of FE extract on male C57BL/6J mice. Bodyweight of each mouse was measured from the same groups in Example 7. There was no statistical difference among the three groups of basal bodyweight. After 16 weeks of treatment, all the mice in the high-fat treated groups (group 2 and 3) had gained significantly more bodyweight than those in the low-fat treated group. However, the extent of bodyweight gain in the FE group was much lower as compared to positive control group, indicating an activity of FE extract on bodyweight control (FIG. 5).

Example 9

Figures 1, 2, 3, 4, 5, 6:
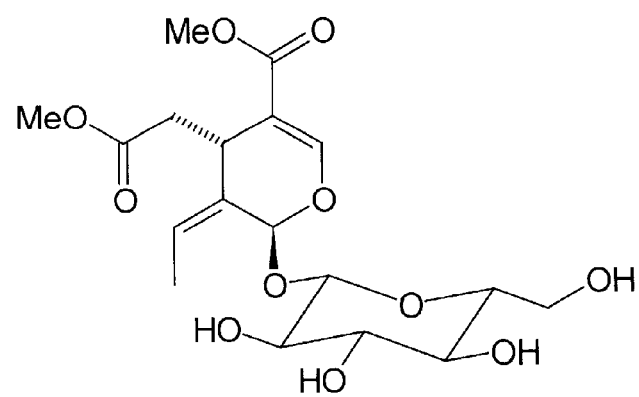
Figure 3:
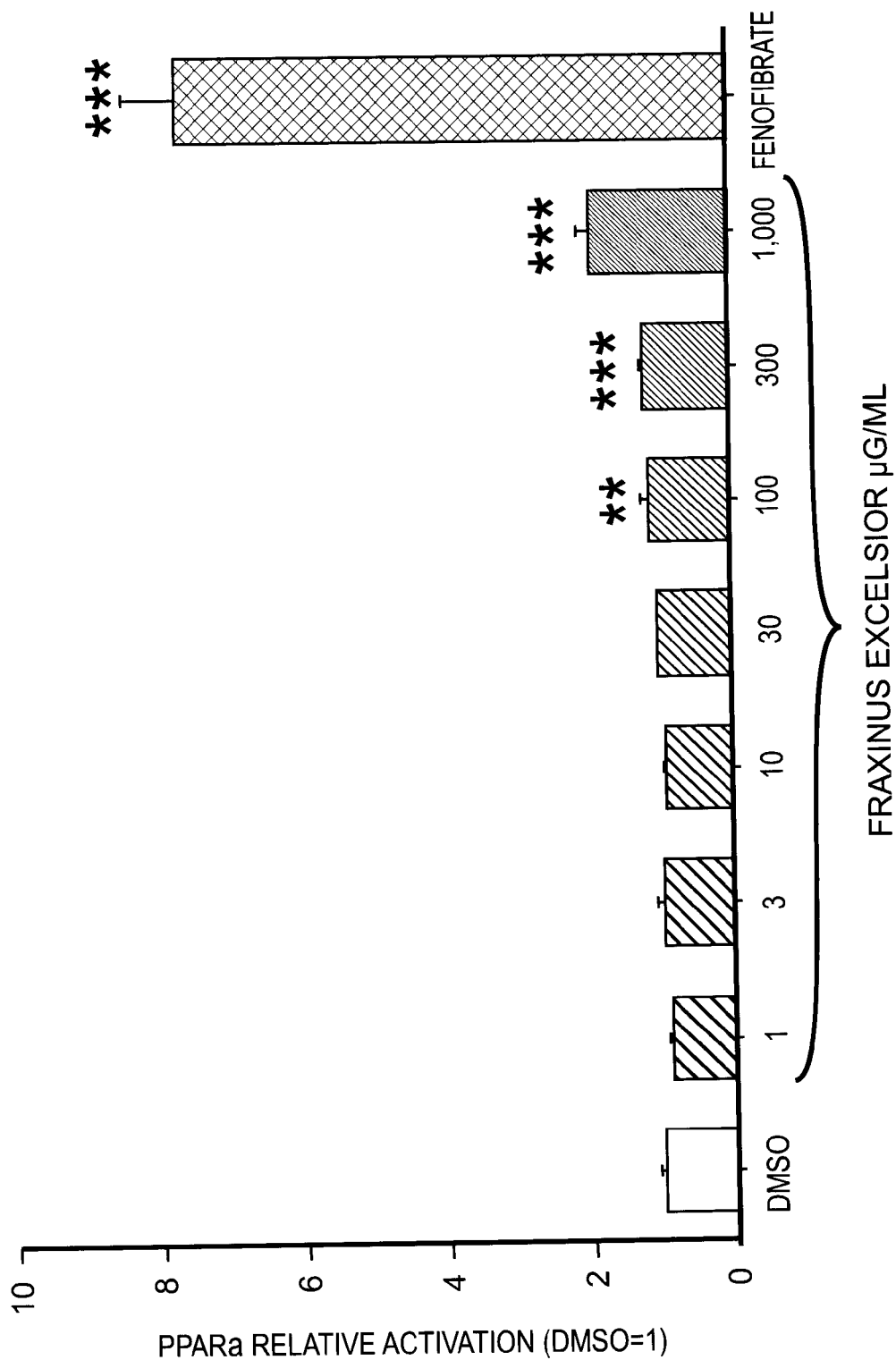
Figure 4:
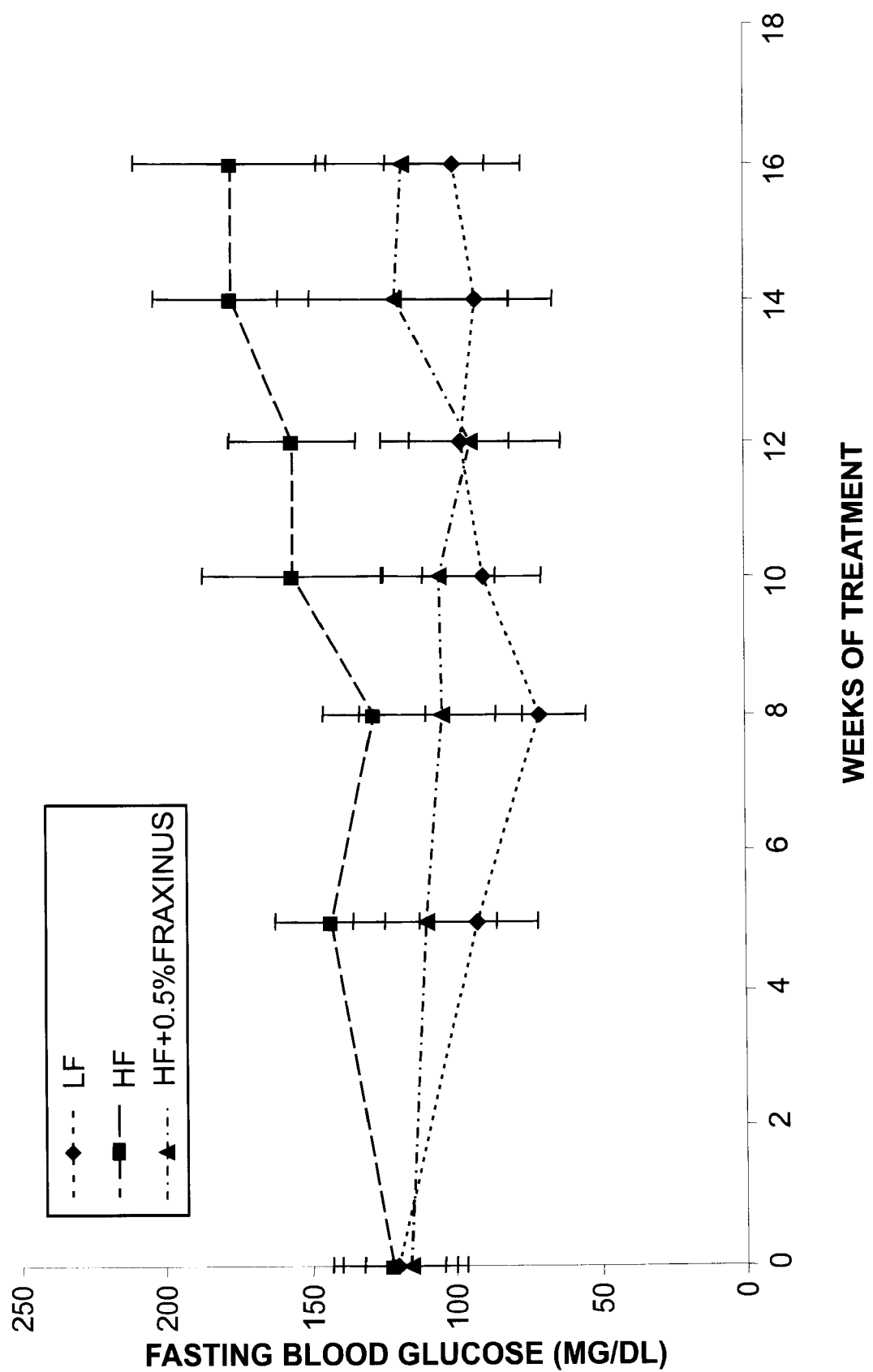
Figure 5:
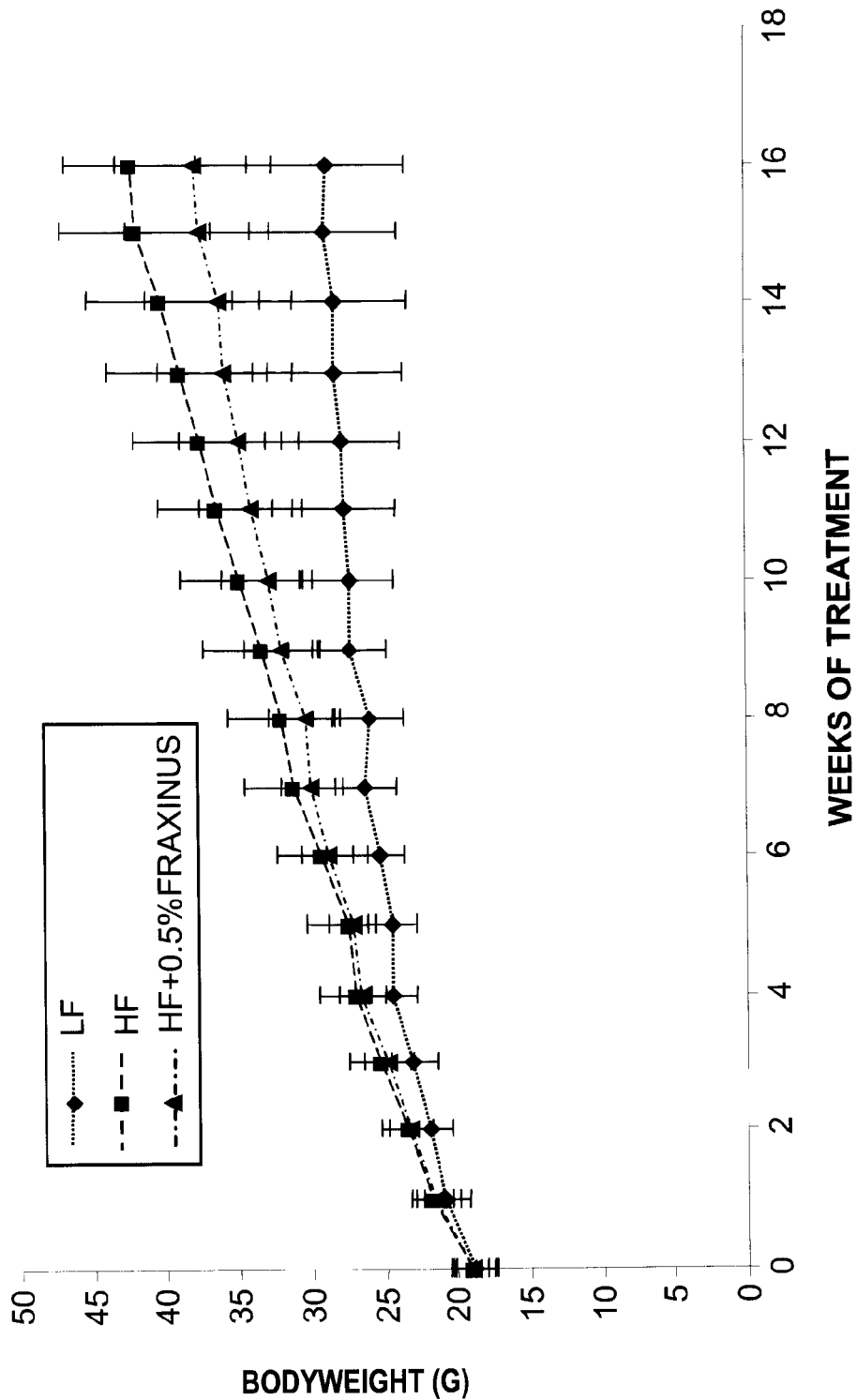
Figure 6:
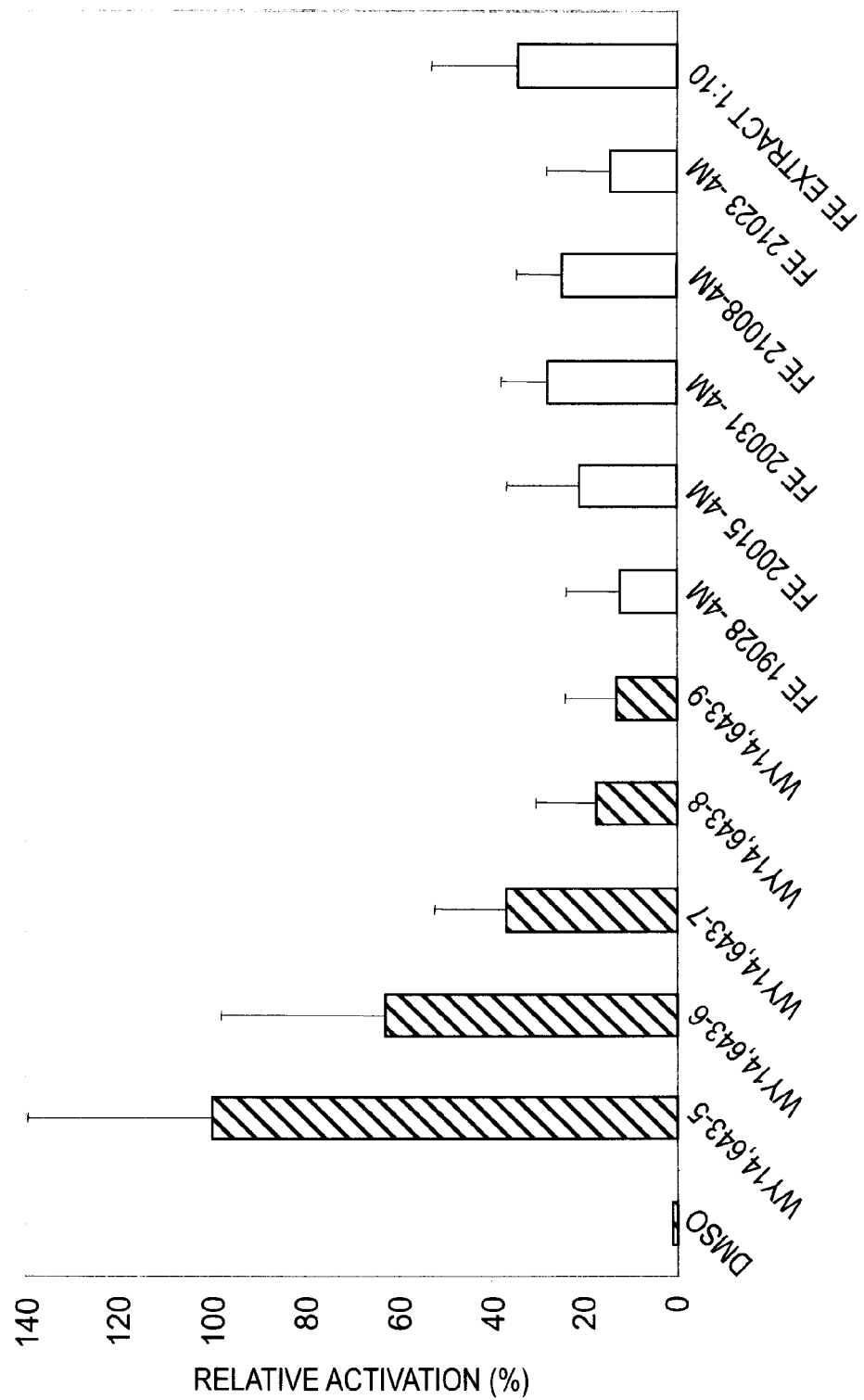

PPAR-alpha activity of excelside A (1), GI3 (4), and oleoside dimethyl ester (6). Five single compounds isolated from *Fraxinus excelsior* (FE) seed water extract were tested for PPAR-alpha activity. The synthetic and selective PPAR alpha activator WY14,643 served as positive control and DMSO which was used to dissolve these compounds as negative control in the assay. Five pure secoiridoids were partly active at a concentration of $10^{-4}$ M. Compounds excelside A, oleoside dimethyl ester, and GI3 showed good activity (FIG. 6).

Example 10

Figure 7:
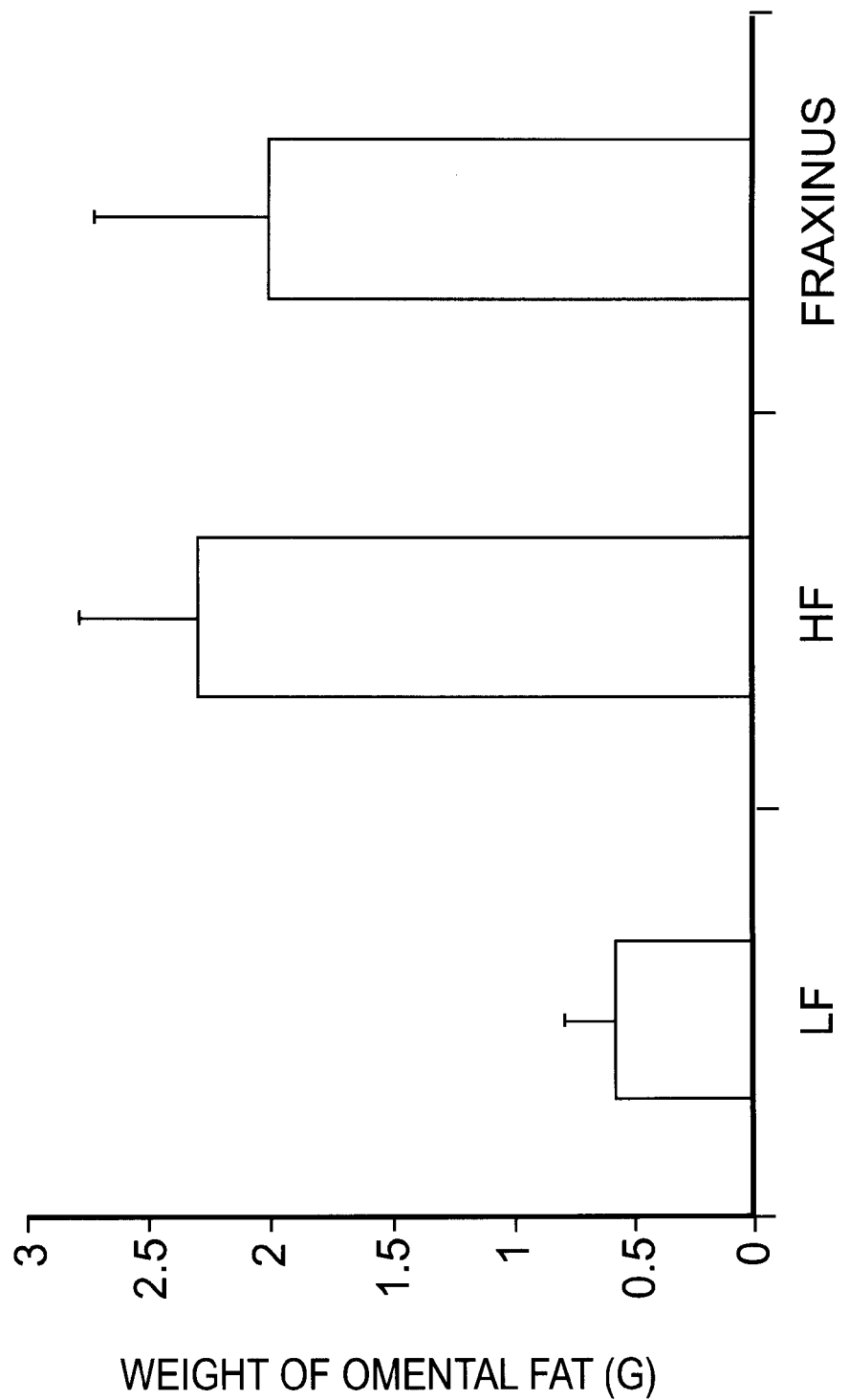
FIG. 7 illustrates the weight (g) of the omental fat from individual mouse from the LF (n=10), HF (n=10), and FE seed extract groups, respectively.
Figure 8:
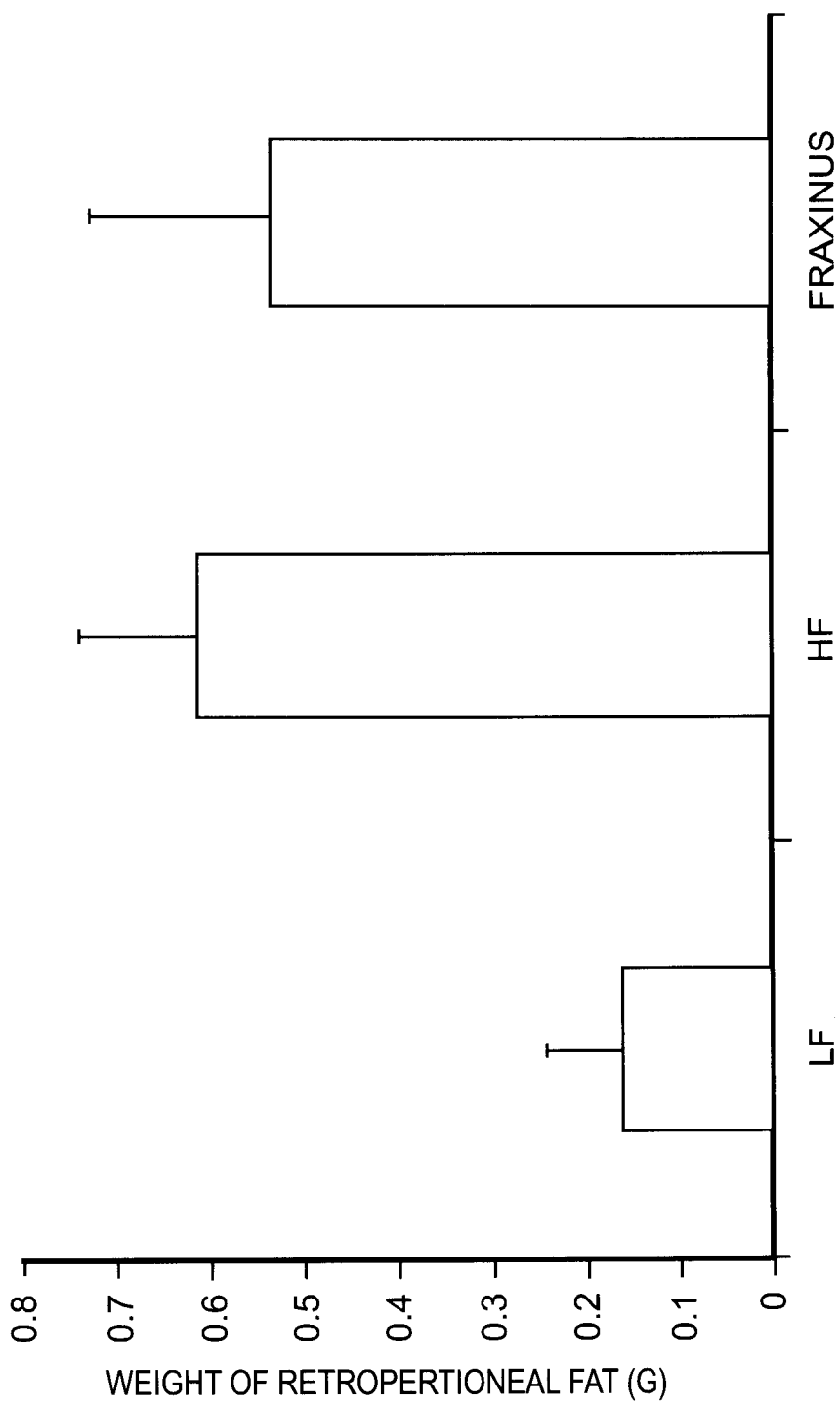
FIG. 8 illustrates the weight (g) of the retroperitoneal fat from individual mouse from the LF (n=10), HF (n=10), and FE seed extract groups, respectively.

Fat reduction of *Fraxinus excelsior* (FE) seed extract on male C57BL/6J mice. At the end of the experiment (from Example 7), after 16 weeks of treatment, the mice from all the groups were anesthetized and sacrificed. The omental and retroperitoneal fat from individual mice were collected and weighed. The results showed that the FE seed extract decreased 18.3% omental fat gain and 17.8% retroperitoneal fat gain, respectively, (FIGS. 7 and 8).

Example 11

Figure 9:
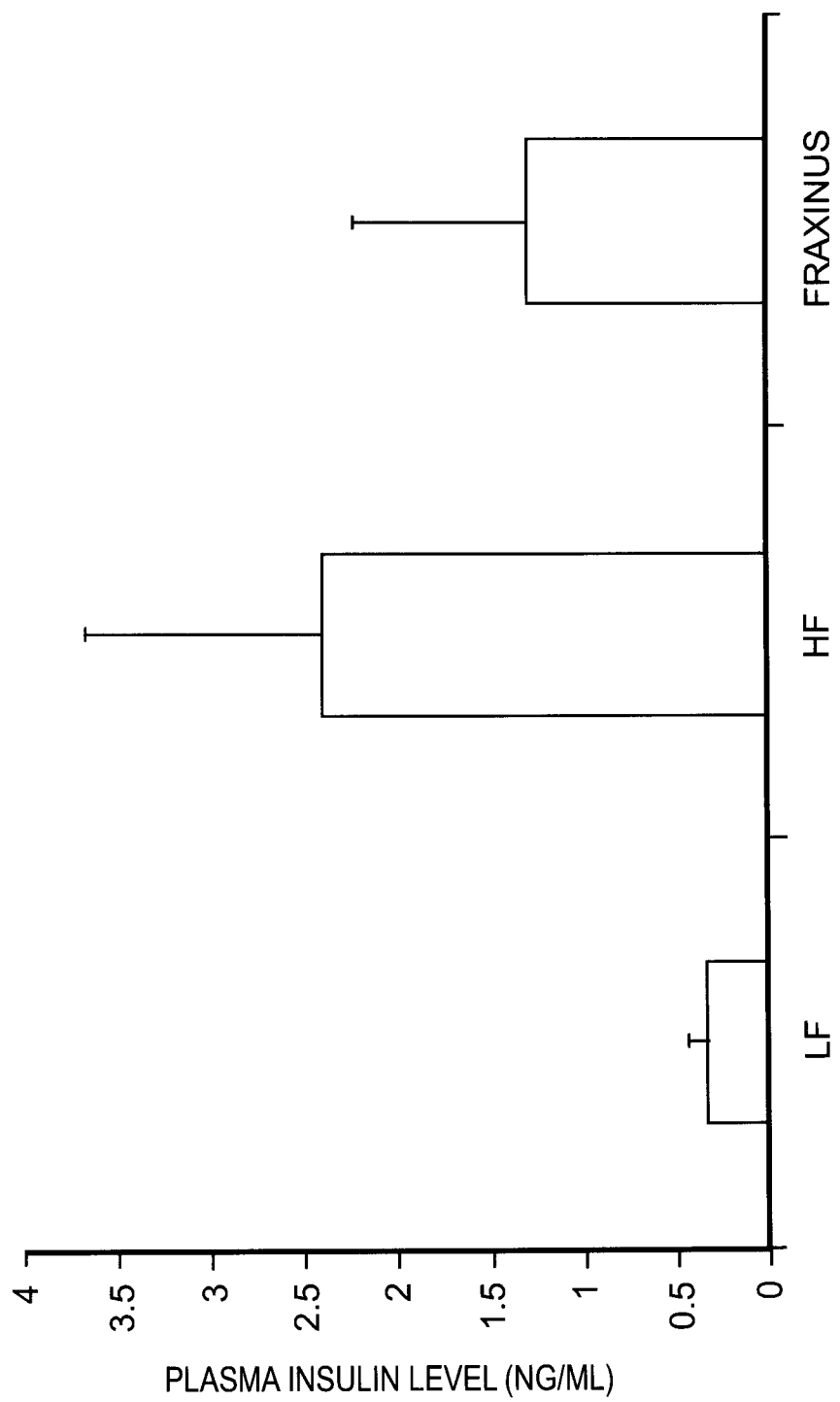
FIG. 9 illustrates the fasting plasma insulin levels (ng/mL) from individual mouse from the LF (n=10), HF (n=10), and FE seed extract groups, respectively.

Fasting plasma insulin levels reduction of *Fraxinus excelsior* (FE) seed extract on male C57BL/6J mice. At the end of the experiment (from Example 7), fasting plasma insulin levels were determined using mouse Elisa kit. *Fraxinus* seed extract treated mice had significantly lower fasting plasma insulin levels in comparison to those from the high fat control group (P<0.05) (FIG. 9).

Example 12

Blood sugar lowering activity of *Fraxinus excelsior* (FE) seed extract in human. To evaluate the effect of the compositions of this invention in humans, a randomized, double-blind, placebo controlled, and crossover designed study on humans was performed. A total of sixteen healthy individuals (11 males and 5 females) were recruited from India. Subjects were required to be between 25 and 55 years of age with body mass index 26±2.2 kg/m² and fasting blood glucose 4.4±0.09 mmol/L. FE seed extract was used for the treatment group and wheat bran powder was used for the placebo group. The daily dosage per person in this study was 1 g of FE seed extract. Subjects were instructed either to take two capsules of FE seed extract (500 mg each) or two capsules of placebo (500 mg of wheat bran each) orally as a single dose prior to the glucose challenge (50 g in 100 mL water) for evaluation of glycemic response. After a one week washout period, the two groups were switched with each other. During the study, finger-prick blood samples were obtained at 0, 15, 30, 45, 60, 90 and 120 minutes. The test extract/placebo was given with 100 mL of water immediately after taking the fasting blood sample at 0 min. Subject then ingested the glucose drink within 5-8 minutes (50 g in 100 mL of water, D-glucose, Qualigens Co., Glaxo India). At this moment the timer was started. Additional finger-prick blood samples were taken at 15, 30, 45, 60, 90 and 120 min after the start of glucose drink. Glucose concentrations were determined in whole blood in the capillary using Bayer's glucometer and Essentia glucotrip. The positive incremental Area Under the Curve (AUC) for both placebo and FE treated groups was calculated for blood glucose concentrations at different time intervals. Significant differences between groups were calculated using a two-tailed paired Student's t-test. Analyses were performed using XLSTAT 2008 software (Addinsoft™, USA). Statistical significance was set at P<0.05. All data are reported as mean±SEM.

Figure 10B:
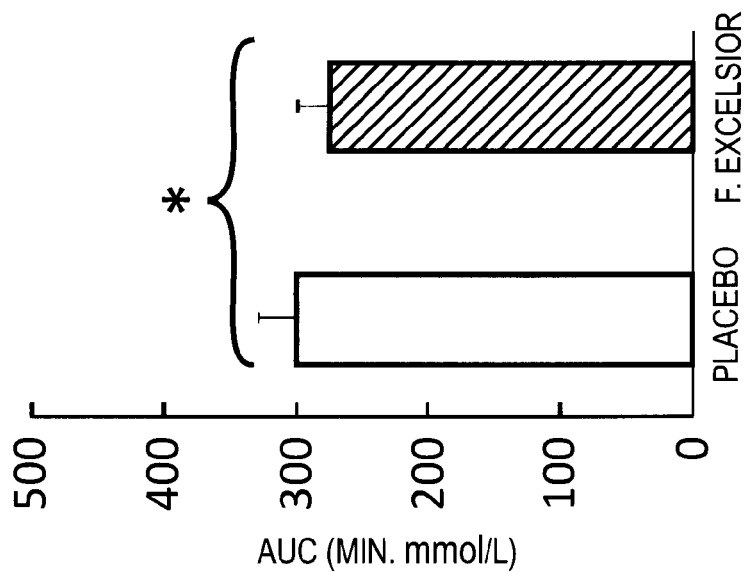
FIGS. 10A and 10B respectively illustrate a comparison (mmol/L versus time) between *Fraxinus excelsior* L seed extract (FE) (1.0 g) and matched wheat bran placebo (1.0 g) on glycemia in healthy volunteers administrated with 50 g of glucose, for (A) incremental glycemia at individual time points, and (B) area under the blood glucose curve (AUC), with values being mean±SEM. *P=0.02, paired Student's t test (n=16)
Figure 10A:
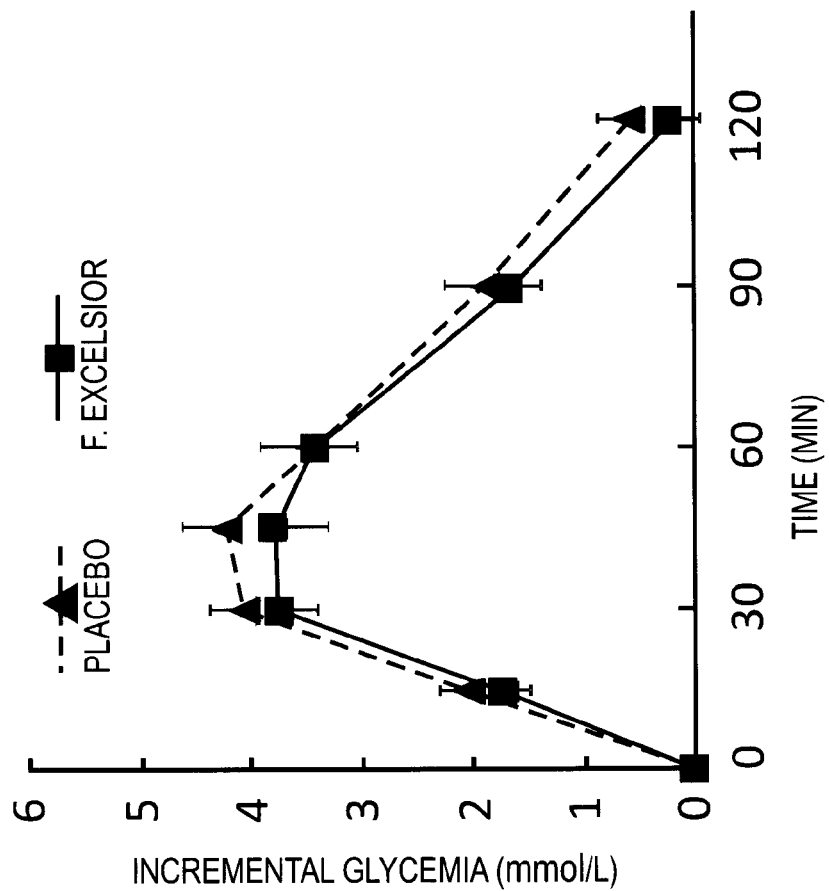

The graphic, from pair-wise comparison, of incremental glycemia showed decrease in postprandial glucose levels by FE seed extract, during the duration of the experiment from 15 min (2.0±0.26 mmol/L vs 1.7±0.21 mmol/L), 30 (4.0±0.41 mmol/L vs 3.7±0.33 mmol/L), 45 (4.2±0.41 mmol/L vs 3.7±0.47 mmol/L), 60 (3.4±0.46 mmol/L vs 3.4±0.41), 90 (1.8±0.38 mmol/L vs 1.6±0.31 mmol/L) to 120 (0.58±0.29 mmol/L vs 0.21±0.27 mmol/L) minutes as compared to matched wheat bran placebo (FIG. 10A). Paired Student's t-test indicated that differences (299.8±28.8 min. mmol/L vs 273.2±25.2 min. mmol/L) in the effect of treatment (FE vs. placebo) on mean AUC were statistically significant (P=0.02). The results are presented in FIG. 10B.

Example 13

Figure 11B:
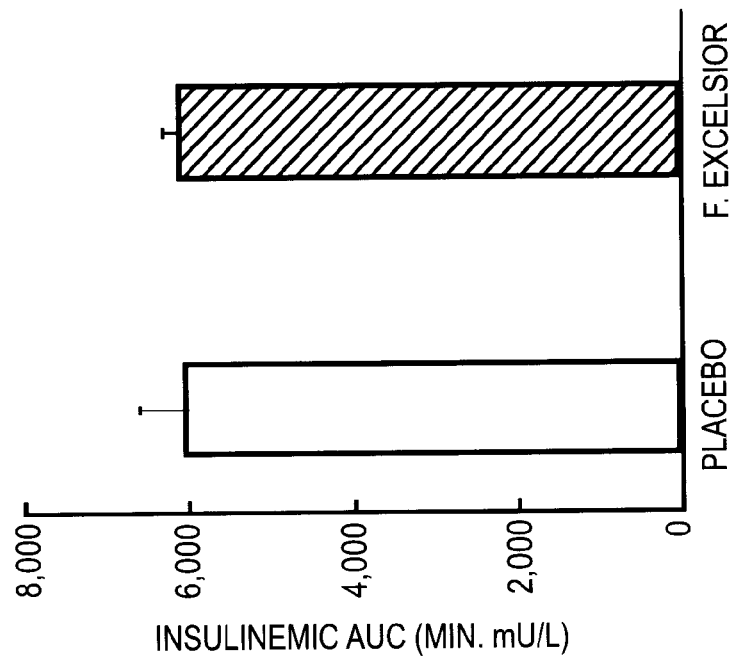
FIGS. 11A and 11B respectively illustrating a comparison (mU/L versus time) between *Fraxinus excelsior* L seed extract (1.0 g) and matched wheat bran placebo (1.0 g) on insulin levels in healthy volunteers administrated with 50 g of glucose, for (A) incremental insulinemia at individual time points, and (B) insulinemic area under the curve (AUC), with values being mean±SEM. **P=0.002, Student's t test (n=16).
Figure 11A:
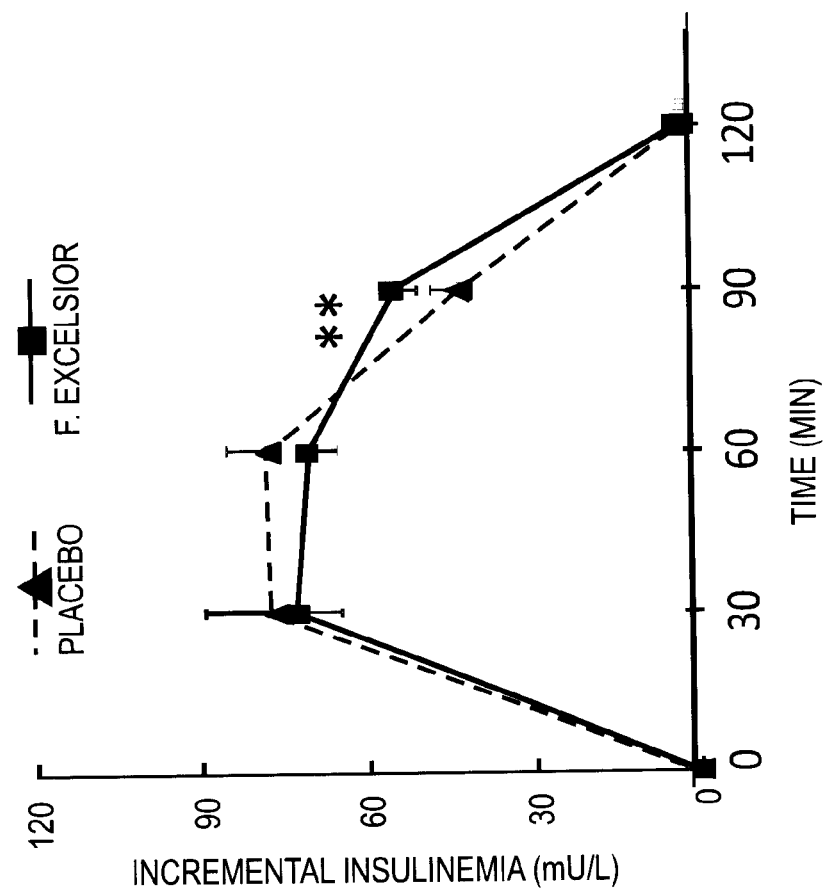

Acute insulinotropic effect of *Fraxinus excelsior* (FE) seed extract on humans. The insulinotropic effect of the composition was evaluated as an additional objective of the clinical study described in Example 12. Venous blood samples (7-8 mL) were collected at 0, 30, 60, 90 and 120 min in test FE/placebo of treated healthy subjects in serum separator tubes. The blood was allowed 15 minutes to clot, and then was centrifuged at 1,500×g for 10 minutes. The resulting serum was then analyzed for insulin using an electro chemiluminescence immunoassay (ECLIA). The positive incremental insulinemic Area Under the Curve (AUC) for both placebo and FE treated groups was calculated for insulin levels at different time intervals. Significant differences between groups were calculated using a two-tailed paired Student's t-test. Analyses were performed using XLSTAT 2008 software (Addinsoft™, USA). Statistical significance was set at P<0.05. All data are reported as mean±SEM. FE (55.5±4.6 mU/L) induced a significant (P=0.002) secretion of insulin at 90 minutes compared to placebo (43.5±5.0 mU/L) (FIG. 11A). No significant difference was noticed in the mean insulinemic AUC (0-120 minutes), in FE treated group (6,041.6±340.5 min.mU/L) compared to placebo (5,996.3±594.58 min.mU/L) (FIG. 11B).

The stimulation of insulin secretion at 90 min seems to be a direct action of the FE on the pancreatic islet cells which returned to normalcy at the end of the study (120 minutes). This may reduce insulin resistance and improve insulin sensitivity in such cases. Further, since there is no significant difference in mean insulinemic AUC between treatment and placebo, the use of extract is safe with no resultant hyperinsulinemia in the following hours post treatment.

It should be understood that the effective amount of the FE extract can vary depending upon the weight of the animal or person taking the treatment, as is known to persons of ordinary skill in the art. Further, the FE extract may be delivered by any conventional medium, in a formulation resulting in a liquid, powder, or caplet, tablet or capsule or other conventional medicament form, together with such fillers, additives, binders, excipients, flavors and the like, as are commonly used in over-the-counter pharmaceutical and dietary supplement products.

One skilled in the art will appreciate that the present invention can be protected by other than the embodiments described, and the numerical quantities and ranges given, which are provided for purposes of illustration, and not of limitation.

We claim:

1. A method of reducing bodyweight in a human subject comprising administering an amount of a *Fraxinus excelsior* seed extract effective to treat said human subject; wherein said *Fraxinus excelsior* seed extract comprises an isolated secoiridoid nuzhenide and an isolated secoiridoid GI3.

2. The method of claim 1 wherein said *Fraxinus excelsior* seed extract further comprises a pharmaceutical dietary supplemental ingredient selected from the group consisting of fillers, additives, binders, flavorings and mixtures thereof.

3. The method of claim 1, wherein said *Fraxinus excelsior* seed extract is administered in a liquid form.

4. The method of 1, wherein said *Fraxinus excelsior* seed extract is administered in a powder form.

5. The method of claim 1, wherein said *Fraxinus excelsior* seed extract is administered in a caplet form.

6. The method of claim 1, wherein said *Fraxinus excelsior* seed extract is administered in a tablet form.

7. The method of claim 1, wherein said *Fraxinus excelsior* seed extract is administered in a capsule form.

\* \* \* \* \*

UNITED STATES PATENT AND TRADEMARK OFFICE
CERTIFICATE OF CORRECTION

PATENT NO. : 8,142,826 B2  
APPLICATION NO. : 12/185649  
DATED : March 27, 2012  
INVENTOR(S) : Kan He et al.

Page 1 of 1

It is certified that error appears in the above-identified patent and that said Letters Patent is hereby corrected as shown below:

TITLE PAGE

Insert
-- Related U.S. Application Data
(60) Provisional application No. 60/985,558, filed on Nov. 5, 2007. --

In Column 3, Line 57, delete "Annu Rev Nuir" and insert -- Annu Rev Nutr --, therefor;

In Column 6, Line 44, delete "4.8 (d, J=8.0 Hz, H-1)" and insert -- 4.8 (d, J=8.0 Hz, H-1') --, therefor;

In Column 7, Line 2, delete "#-configuration" and insert -- β-configuration --, therefor;

In Column 7, Line 14, delete "+,β-unsaturated" and insert -- α,β-unsaturated --, therefor;

In Column 10, Line 3, delete "(aa1 80-464)" and insert -- (aa180-464) --, therefor.

Signed and Sealed this
Eighth Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,142,826 B2  Page 1 of 1
APPLICATION NO. : 12/185649
DATED : March 27, 2012
INVENTOR(S) : Kan He et al.

It is certified that error appears in the above-identified patent and that said Letters Patent is hereby corrected as shown below:

On the title page,

Assignee "NATUREX, INC." should be changed to -- NATUREX, S.A. --.

City and State/Country of the Assignee "SOUTH HACKENSACK, NJ (US)" should be changed to -- Montfavet, Avignon (FR) --.

Signed and Sealed this
Seventh Day of August, 2012

David J. Kappos
*Director of the United States Patent and Trademark Office*